United States Patent

Kim

[11] Patent Number: 6,111,602

[45] Date of Patent: *Aug. 29, 2000

[54] METHOD AND APPARATUS FOR INSPECTING SOLDER JOINTS

[75] Inventor: Jong Hyung Kim, Sungnam, Rep. of Korea

[73] Assignee: Samsung Electronics Co., Ltd., Suwon, Rep. of Korea

[ * ] Notice: This patent issued on a continued prosecution application filed under 37 CFR 1.53(d), and is subject to the twenty year patent term provisions of 35 U.S.C. 154(a)(2).

[21] Appl. No.: 08/769,522

[22] Filed: Dec. 19, 1996

[30] Foreign Application Priority Data

Dec. 28, 1995 [KR] Rep. of Korea .................. 95-61661

[51] Int. Cl.[7] .................................................. H04N 7/18
[52] U.S. Cl. .............................................. 348/92; 382/145
[58] Field of Search .................. 348/92, 95, 88, 348/87, 145, 90, 126; 382/145, 131, 156, 150, 144, 147, 157; 228/102

[56] References Cited

U.S. PATENT DOCUMENTS

| | | | |
|---|---|---|---|
| 5,064,291 | 11/1991 | Reiser | 348/131 |
| 5,293,178 | 3/1994 | Kobayashi | 348/92 |
| 5,365,084 | 11/1994 | Cochran et al. | 348/88 |
| 5,377,278 | 12/1994 | Ichikawa | 348/92 |
| 5,542,600 | 8/1996 | Kobayashi et al. | 228/102 |
| 5,699,449 | 12/1997 | Javadi | 382/156 |
| 5,751,910 | 5/1998 | Bryant et al. | 382/145 |
| 6,023,663 | 2/2000 | Kim | 382/150 |

*Primary Examiner*—Chris S. Kelley
*Assistant Examiner*—Gims Philippe
*Attorney, Agent, or Firm*—Burns, Doane, Swecker & Mathis, L.L.P.

[57] ABSTRACT

A method and apparatus for inspecting solder joints are provided. A method for inspecting test solder joints includes the steps of illuminating the test solder joints on a printed circuit board to obtain sample images of the test solder joints by grabbing reflected light with a charge coupled device (CCD) camera, classifying the sample images by an inspector into a number of classes according to the soldering quality, inputting a specific sample image belonging to each class to a neural network to divide the class into a predetermined number of clusters; determining a synaptic weight of each class by learning each cluster, determining a confirmed synaptic weight by adjusting the synaptic weight according to a boundary condition between the clusters belonging to neighboring different classes, and selecting a similar cluster by comparing the similarities between the outputs of the neural network with respect to the test solder joints based on confirmed synaptic weights, and each output of the inspector's class. The method and apparatus for inspecting solder joints can guarantee satisfactory classification accuracy with the minimum number of prototype images.

3 Claims, 4 Drawing Sheets

| CLASSIFICATION OF SOLDER JOINT QUALITY | 3-D SHAPES | TYPICAL COLOR PATTERNS |
|---|---|---|
| I |  |  |
| IA |  |  |
| A |  |  |
| EA |  |  |
| E |  |  |

METHOD AND APPARATUS FOR INSPECTING SOLDER JOINTS

BACKGROUND OF THE INVENTION

The present invention relates to a method and apparatus for inspecting solder joints, and more particularly, to a method and apparatus for inspecting solder joints on a printed circuit board (PCB) by using a circular illumination technique and a neural network classifier.

The solder joints of surface mounted components on a PCB appear in various three-dimensional (3D) shapes according to the quantity of soldering material and a soldering temperature condition, etc. Moreover, the surfaces of the solder joints are specular. To judge the soldering quality of the solder joints, there have been proposed various neural network based methods. By these known methods, the specular surfaces of the solder joints are illuminated with a lamp or lamps, light reflected from the specular surface is received in a charge coupled device (CCD) camera to acquire digitized image data of the received 3D shape information of the solder joints. The acquired 3D image data is learned and classified in a neural network by an artificial intelligence technique to recognize the shape of the solder joints, and thereby determine the soldering quality of the solder joints.

However, such a conventional neural network learning and classification method is typically based on an unsupervised version of Kohonen's learning vector quantization (LVQ) algorithm, which requires a large number of prototypes to insure satisfactory classification accuracy, thereby lowering the overall efficiency of the learning and classification process. In practice, self-organized clusters or self-organized prototypes generated in the neural network based learning process are just a measure for judging the similarity between respective test materials. As a result, the case where the inspector's intention does not correspond to the designer's.

Meanwhile, a conventional illumination method employs a plurality of lamps and to a single camera or a plurality of cameras and a single lamp, to measure the slope of the surfaces of solder joints. Here, either of the lamp(s) or the camera(s) is moved in order to acquire the image data. In such an illumination method, since various images should be recorded and analyzed every time a lamp or a camera is moved, much processing time is not only consumed but also expensive equipment is required.

SUMMARY OF THE INVENTION

Therefore, to solve the above problems, it is an object of the present invention to provide a solder joint inspection method and apparatus which has enhanced classification accuracy using a minimum number of prototypes based on an adaptive learning vector quantization (LVQ) method.

It is another object of the present invention to provide a method and an apparatus for inspecting solder joints in a short processing time with low-priced equipment by using a circular illumination technique.

To accomplish the above object of the present invention, there is provided a method for inspecting test solder joints, the method comprising the steps of: illuminating the test solder joints on a printed circuit board to obtain sample images of the test solder joints by capturing reflected light with a charge coupled device (CCD) camera; classifying the sample images by an inspector into a number of classes according to the soldering quality; inputting a specific sample image belonging to each class to a neural network to divide the class into a predetermined number of clusters; determining a synaptic weight of each class by learning each cluster; determining a confirmed synaptic weight by adjusting the synaptic weight according to a boundary condition between the clusters belonging to neighboring different classes; and selecting a similar class by comparing the similarities between the outputs of the neural network with respect to the test solder joints based on confirmed synaptic weights and each output of the inspector's class.

Here, in the step of adjusting the synaptic weights, if the input of another class takes the synaptic weight already assumed by a specific class, it is desirable that the synaptic weight of the latter is altered in the direction moving away from the input.

In the step of determining the synaptic weights, if the similarity between the synaptic weight of a current input and a preset winner synaptic weight based on a previous input is larger than a predetermined range, it is preferable that a new output neuron is generated.

The illumination apparatus includes a number of different colour lamps which illuminate the surface of solder joints at different incident angles, wherein a single CCD camera can receive the reflected light created by each lamp.

There is also provided an apparatus for inspecting solder joints comprising: illumination means for illuminating the solder joints; a CCD camera which captures reflected light created by the illumination means; an image grabber which digitizes an image of the CCD camera into digital frame data; and a main processor with a neural network which confirms the synaptic weight of each class by learning the data input from the image grabber by each class supervised by the inspector.

Here, the illumination means can simply be comprised of a plurality of circular colour lamps which have different incident angles.

Preferably, the colour lamps are of high-frequency fluorescent lamps, which have green, red and blue colours. Also, the colour lamps are preferably coaxially tiered with a CCD camera located axially at the top of the lamps.

DETAILED DESCRIPTION OF THE PREFERRED EMBODIMENT

An embodiment of the present invention will be described with reference to the drawings.

Figure 1:
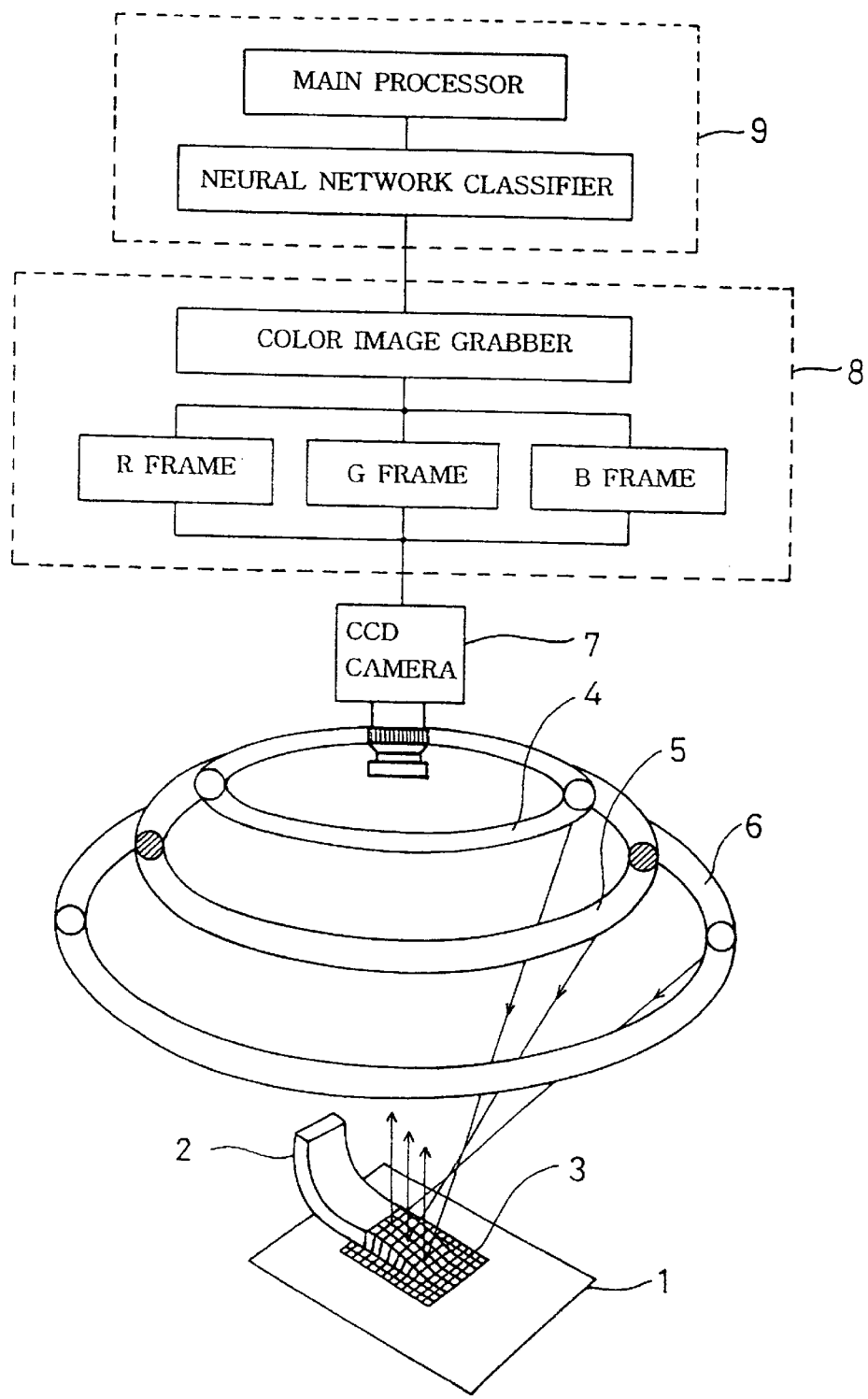
FIG. 1 is a schematic perspective view of an illumination system employed to acquire an image the solder joints in a solder joint inspection apparatus according to the present invention.

FIG. 1 is a schematic perspective view of an illumination system employed to acquire an image of solder joints in a solder joint inspection apparatus according to the present invention. As can be seen from FIG. 1, a lead 2 of a surface mounted component is attached on a printed circuit board (PCB) 1 by means of a solder joint 3. Three colored circular lamps 4, 5 and 6 which have different diameters, are coaxially tiered over the solder joint 3. The light illuminated from the colored lamps 4, 5 and 6 is reflected from the specular surface of the solder joint 3 to be picked up by a CCD camera 7 which is located the solder joint 3. The colored circular lamps 4, and 6 are high-frequency fluorescent lamps which are preferably tiered in the sequence of green (G), red (R), and blue (B) moving upward from an inspection surface. Due to the different heights and diameters of the lamps, incident angles with respect to the solder joint are different. Thus, different color images can be obtained depending on the slope of surface of solder joints. For example, when the uppermost blue color lamp 4 having the smallest diameter illuminates the solder joint 3 at an angle of 20° with respect to a vertical line of the PCB 1, the red color lamp 5 illuminates the solder joint 3 at an angle of 40° and the green color lamp 5 illuminates the solder joint 3 at an angle of 70°, the surface of the solder joint having the slope of an angle around 10° is seen as blue in one frame of image which has been obtained as described above; the surface having a gentle slope of an angle around 20° is seen as red; and the surface having a steep slope of an angle around 35° is seen as green. Because such a color image contains the 3D information of solder joint shapes, a real shape of the solder joint can be extracted from the color image.

The information obtained by the CCD camera by using circular illumination is transferred to a color image grabber 8 in the form of an electrical signal, and then is converted into quantitative information of a color image composed of each color frame. The above information is stored in the memory of a main processor 9, and classified via a learning process in a neural network classifier of the main processor 9.

Figure 2:
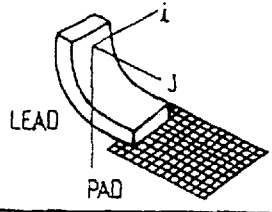
FIG. 2 is a table illustrating classification, 3D shapes and typical colour images for various solder joints.
Figure 2:
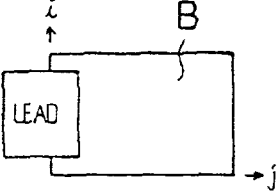
Figure 2:
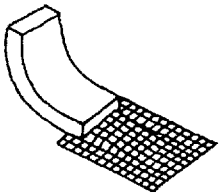
Figure 2:
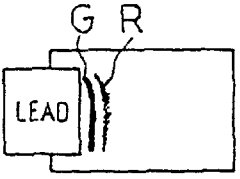
Figure 2:
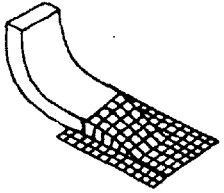
Figure 2:
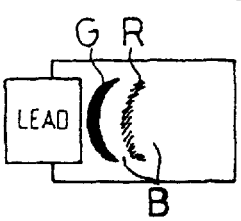
Figure 2:
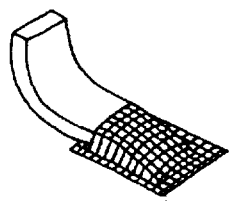
Figure 2:
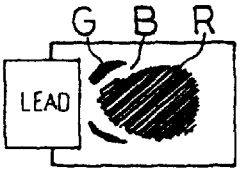
Figure 2:
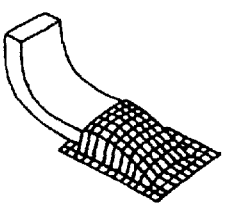
Figure 2:
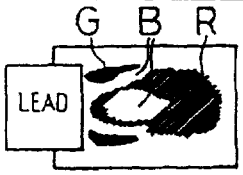

Before performing a neural network classifying process, a large number of colour images of solder joints are extracted, and the qualities of the solder joints are classified by an expert inspector. For example, the qualities are classified into five classes: insufficient soldering (I); insufficient but acceptable soldering (IA)l; acceptable soldering (A); excess but acceptable soldering (EA); and excess soldering (E). FIG. 2 shows typical soldering joint examples of the five classes and of their colour patterns appearing in the color images, where blank represents blue color, oblique line represents red, and black represents green.

The blue (B) pattern appears dominantly in the insufficient soldering (I) image. In the insufficient but acceptable soldering (IA), the red (R) and green (G) patterns begin to appear. In the acceptable soldering (A), the green (G), red (R) and blue (B) patterns appear sequentially. In the excess but acceptable soldering (EA), red (R) pattern appears dominantly in the image. The excess soldering joint (E) has a convex solder fillet, and thus the blue (B) pattern is enclosed by the red (R) and green (G) patterns.

Such an image of the test solder joint which is classified by the expert inspector is input into a neural network, and subjected to a learning process.

The algorithm according to the present invention is based on a supervised version of LVQ (Learning Vector Quantization) and has two learning phases: LVQ1 and LVQ2. In LVQ1, as mentioned above, a self-clustering module is applied to each supervised class classified by the expert inspector, to self-produce a number of clusters. Such a self-clustering module is applied to all the classes to produce the self-organized clusters. The self-organized clusters do not yet form accurate boundaries between each other. Thus, in LVQ2, the boundaries are precisely adjusted with respect to clusters formed in the other classes to insure classification accuracy. The adjusted result is expressed as a weight value connected with one neuron, in which the weight value has the same dimension as that of the input, which is called a prototype image.

Figure 3:
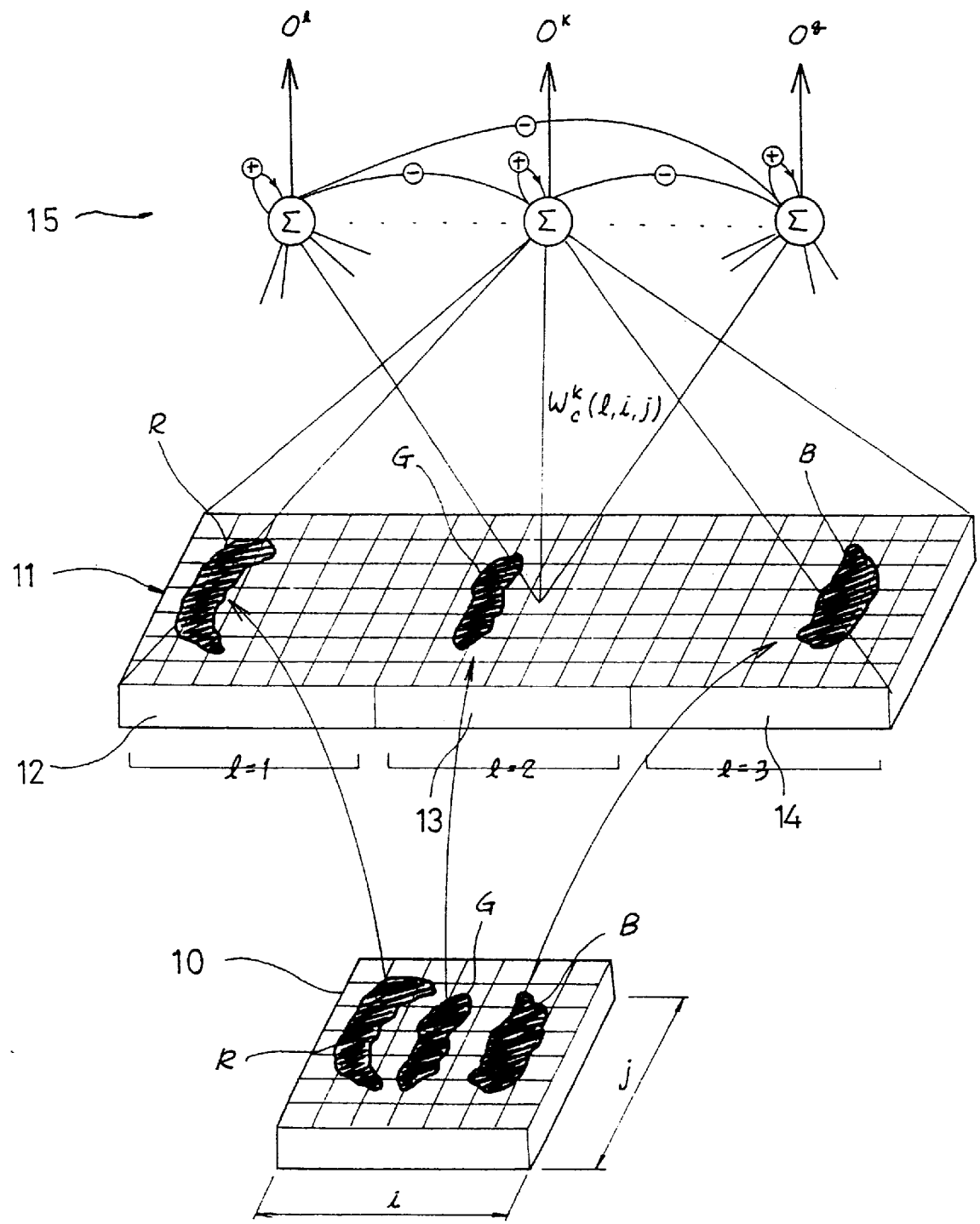
FIG. 3 is a view illustrating a self-organized cluster module adapted in each supervisor classification class.

The structure of the self-clustering module to be applied to each expert inspector classification class is shown in FIG. 3. An input of each color image which is stored in the digital memory is composed of a pixel (i,j) where three colour patterns: the red, green and blue patterns are formed. Each color pattern is divided into each color frame 12, 13 or 14 having the same magnitude as that of the input image. Thus, a color intensity of each pixel is used as an input value of an input node 11. The input color image can be represented by:

$$I_c = \{I_c(l,i,j) | l=1,2,3.\ i=1,2,\ldots, n\ j=1,2,\ldots, m)\} \quad (1)$$

where subscript c indicates the class of the input image, $I_c(l,i,j)$ means an intensity value at the (i,j) pixel in the lth digital memory frame, that is, l represents an index of each color (1=red, 2=green, 3=blue), and (n,m) indicates the size of the image. One image ic composed of n =m pixels.

The dimension of the input nodes is the same as that of the input winner images. Output neurons 15 are fully connected to all input nodes by the synapses. A set of the synaptic weights between the kth output node and the input nodes is defined as follows:

$$W_c^k = \{W_c^k(l,i,j) | l=1,2,3,\ i=1,2,\ldots, n,\ j=1,2,\ldots, m\} \quad (2)$$

where all subscripts are the same as those of the input image. The input value of the kth output neuron is a correlation value of a brightness value of the input image and the synaptic weights, which is expressed by:

$$S^k = W_c^k \cdot O_c = \sum_i^n \sum_j^m \sum_l^3 W_c^k(l i, j) \cdot I_c(l, i, j) \quad (3)$$

In the self-clustering module, the input value of the output node 15 indicates the mutual similarity, that is, a degree of resemblance between the brightness value of an input image and the synaptic weights. As shown in FIG. 3, the output value of each neuron is positively feedback to itself and negatively feedback to the other output neurons. Then, only one neuron with the maximum output value converges to a positive value, and the others converge to zero, which is a principle of a competitive learning mechanism. In other words, only one output neuron connected with the synaptic weight which is nearest to the brightness value of the current input image is selected as a "winner." The synaptic weights of the winner are to be learned towards resembling the input image.

In the practical application of the LVQ algorithm, the number of output neurons directly influences classification accuracy and computational burden. If the number of output nodes is too large, the input images can be precisely classified although processing time is lengthened. On the other hand, if the number of output neurons is too small, it is difficult to ensure a precise classification of the input images although processing time is shortened.

Therefore, it is essential to add an additional mechanism such as an adaptive learning mechanism to reduce the number of output neurons while maintaining a desired accuracy of classification.

An adaptive learning mechanism is designed to obtain the optimal number of the output neurons. The main idea of this mechanism is that if the similarity between a newly input image and a winner to which the input image belongs is less than a threshold, the newly input image is not made to belong to the winner, but an additional output neuron is independently produced to produce another cluster and then to make the newly input image to belong to the produced cluster. A similar idea has been considered by other researchers, who have a great similar interest in the other practical application such as image compression using the LVQ algorithm.

The detailed procedure of training or learning the overall neural network using an adaptive learning mechanism is described as follows.

First, apply a self-clustering module to one of the supervised classes, the cth class. Assign the colour intensity of the first sample image to the synaptic weights of the first output neuron.

$$W_c^k = I_c, \; k=1 \tag{4}$$

Take the next sample image and determine a winner output neuron.

$W_c^{win}$ is a set of the synaptic weighs connected with the winner output neuron. $W_c^{win}$ has the relationship of the following expressions for all k:

$$\sum_i^n \sum_j^m \sum_l^3 |W_c^{win}(l,i,j) - I_c(l,i,j)| < \sum_i^n \sum_j^m \sum_l^3 |W_c^k(k,i,j) - I_c(l,i,j)| \tag{5}$$

where the symbol $|\cdot|$ is an operator for calculating the absolute difference of two scalar values. (When starting, there is only one output neuron.)

Figure 4:
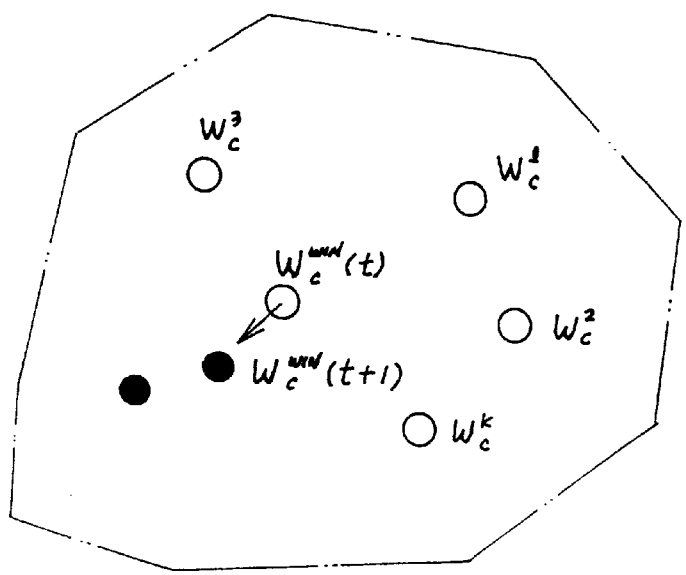
FIG. 4 is a view illustrating a winner prototype image in a first learning vector quantization (LVQ1) phase.

Assign an input $I_c$ to $W_c^{win}$ if the following condition is met:

$$\|W_c^j - I_c\| \leq \xi \times (n \times m \times 3) \tag{6}$$

then, update the synaptic weights of the winner neuron as follows:

$$W_c^{win}(t+1) = W_c^{win}(t) + \eta(t)\{I_c - W_c^{win}(t)\} \tag{7}$$

where t is the number of iterations for learning. $\eta(t)$ is a dynamic learning rate that decreases as t increases. The $\zeta$ is defined as the similarity bound, which determines whether the new input image is assigned to the winner neuron. Its value is determined by the user. The update rule of the equation (7) can be understood in terms of the movement of the winner prototype images in the hypothesis input space, as shown in FIG. 4. By updating the synaptic weights, the winner prototype image moves towards the presented input sample Do not assign the input $I_c$ and the winner neuron $W_c^{win}$ if the following condition is met:

$$\|W_c^{win} - I_c\| \geq \xi \times (n \times m \times 3) \tag{8}$$

which means that the similarity between the input $I_c$, and the winner is less than a reference value. Therefore, a new output neuron is produced and new synaptic weights are assigned as $W_c^{new}$:

$$W_c^{new}(t) = I_c - \eta(t)\{I_c - W_c^{win}(t)\}, \; t=1 \tag{9}$$

Then, the new prototype image has a decision boundary with the winner $W_c^{win}$ in the hypothesis input space. Repeat previous procedures equations (5) through (9) until all test input images have been assigned.

Although the above procedures are finished, the boundary between the prototype images are not clear. Whenever a new prototype image generated, the boundaries between the new one and other existing prototype images should be adjusted. Therefore, the above procedures are repeated until no new prototype image is incremented during this repetition. In the same manner, such a learning process is applied in turn to all supervised classes, respectively.

In LVQ2 learning phase after completing the LVQ1 learning phase, clusters are generated in the supervised classes, and synaptic weights are adjusted by the sample of other classes. The trained synaptic weights in the LVQ1 are used as the initial values of the synaptic weights for the LVQ2.

When a winner is determined via a competition learning method, synaptic weights are changed only if a prototype image of another class is selected as the winner. For example, when an input $I_q$, belongs to the qth class and a winner is found, if the input is misclassified into the cth class, the synaptic weights representative of the cth class are changed as follows:

$$W_c^{win}(t) = W_c^{win}(t) - \eta(t)\{I_q - W_c^{win}(t)\} \tag{10}$$

Figure 5:
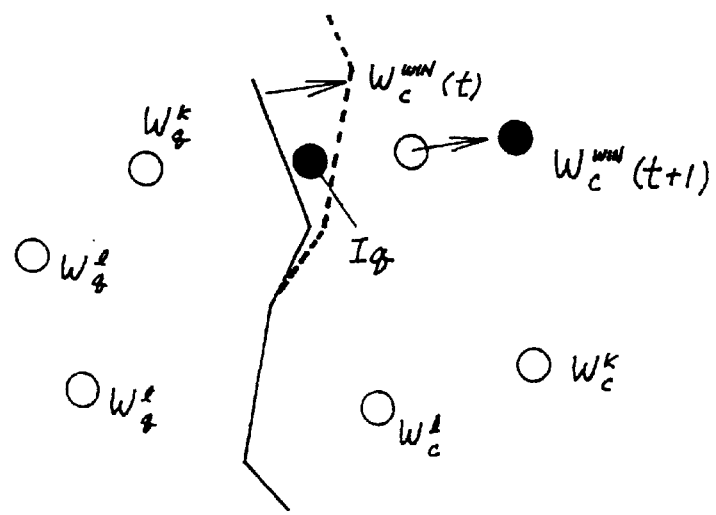
FIG. 5 is a view illustrating a winner prototype image in a second learning vector quantization (LVQ2) phase.

The equation (10) intuitively tells us that when cth class winner is found although the input image 1, belongs to the qth class, the cth class synaptic weights are moved in the opposite direction away from the misclassified input $I_q$, as shown in FIG. 5.

After determining all synaptic weights through the above LVQ1 and LVQ2 learning phases, the synaptic weights are registered as the confirmed synaptic weights.

As shown in FIG. 1, images of solder joints are extracted by using illumination and a CCD camera, the images are input to a an ion system neural network of a main processor, and output values are determined based on the confirmed synaptic weights mentioned above. A supervised class which has an output value similar to such an output is selected, to decide if the solder Joint is assigned to a class which has the best similar output. Accordingly, the solder Joint is assigned to one of the classes which are classified in advance by an expert inspector, and is evaluated as having a quality corresponding to the class.

As described above, according to the present invention, a method and apparatus for inspecting solder joints can guarantee satisfactory classification accuracy with the minimum number of prototype images.

What is claimed is:

1. A method for inspecting solder joints, the method comprising the steps of:

illuminating solder joints on a printed circuit board and obtaining sample images of the solder joints with a charge coupled device (CCD) camera;

classifying the sample images by an inspector into a number of classes according to the soldering quality;

inputting a specific sample image belonging to each class to a neural network to divide the class into a predetermined number of clusters;

determining a synaptic weight of each class by training each cluster;

adjusting the synaptic weight according to a boundary condition between the clusters belonging to neighboring different classes and determining the adjusted synaptic weight as a confirmed synaptic weight; and selecting a similar class by comparing an output of the neural network based on the confirmed synaptic weight and outputs an of inspector's class, wherein the step of determining the synaptic weight includes the steps of generating a new output neuron when the similarity between a current input and a preset synaptic weight based on a previous input is beyond a predetermined range, generating a new cluster when a new output neuron is generated, and causing the current input to belong to the new cluster, and wherein in the step of adjusting the synaptic weights, only when an input of one class takes the synaptic weight of another class, the synaptic weight of the latter is altered in a direction moving away from the input of the former.

2. The method for inspecting solder joints according to claim 1, wherein the illumination is carried out by a plurality of circular lamps having different colours and coaxially arranged to illuminate the surface of the solder joints at different incident angles.

3. The method for inspecting solder joints according to claim 2, wherein the CCD camera is arranged axially relative to the plurality of lamps.

* * * * *